United States Patent [19]

Ishida et al.

[11] 4,256,964
[45] Mar. 17, 1981

[54] GAS ANALYZER

[75] Inventors: Kozo Ishida; Osamu Saitoh; Takao Imaki, all of Miyanohigashi, Japan

[73] Assignee: Horiba, Ltd., Kyoto, Japan

[21] Appl. No.: 972,485

[22] Filed: Dec. 22, 1978

[30] Foreign Application Priority Data

Jan. 10, 1978 [JP] Japan ................................. 53-1726

[51] Int. Cl.³ .......................... G01J 1/00; G01J 1/42
[52] U.S. Cl. ..................................... 250/345; 250/373
[58] Field of Search ............... 250/345, 343, 344, 373; 356/411, 435

[56] References Cited

U.S. PATENT DOCUMENTS

| | | | |
|---|---|---|---|
| 3,449,566 | 6/1969 | Kolb et al. | 250/343 |
| 3,725,702 | 4/1973 | Schaefer | 250/345 |
| 4,180,733 | 12/1979 | Veda | 250/345 |

Primary Examiner—Davis L. Willis
Assistant Examiner—Carolyn E. Fields
Attorney, Agent, or Firm—Wenderoth, Lind & Ponack

[57] ABSTRACT

A gas analyzer includes a first conduit for the supply of gas to be tested, a second conduit for the supply of a standard gas, first and second cells, a light source for directing light rays through the first and second cells, and a detector for receiving the light rays after passing through the cells. There is provided a gas flow changeover device connected to the first and second conduits for alternating at fixed intervals between a first gas supply arrangement wherein fixed amounts of gas to be tested and the standard gas are simultaneously supplied to the first and second cells, respectively, and a second gas supply arrangement wherein the fixed amounts of the gas to be tested and the standard gas are simultaneously supplied to the second and first cells, respectively.

4 Claims, 8 Drawing Figures

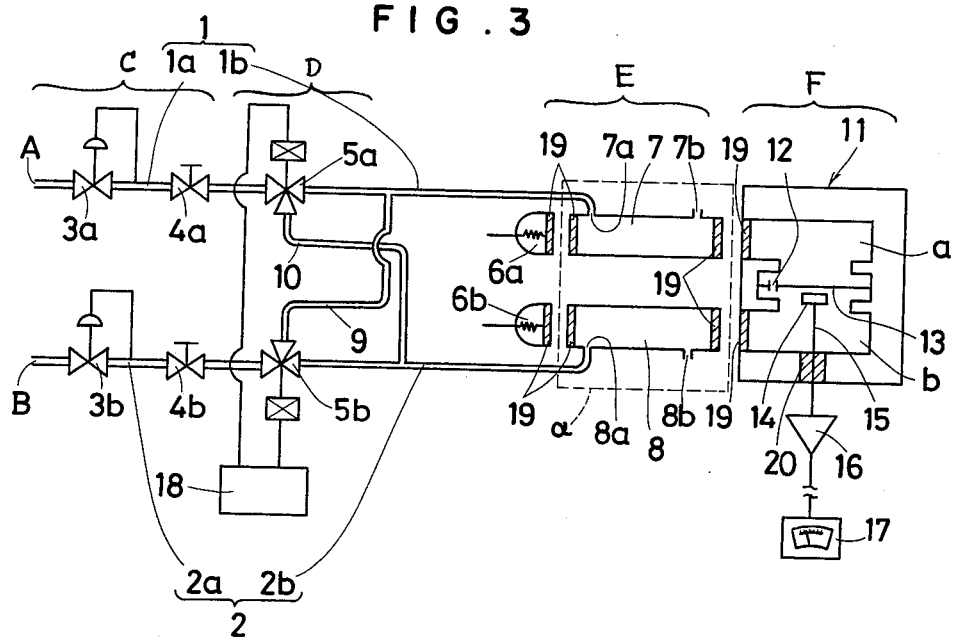
FIG. 3
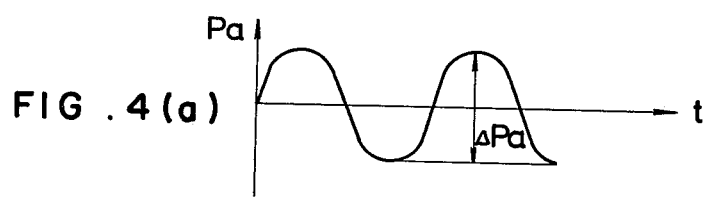
FIG. 4(a)
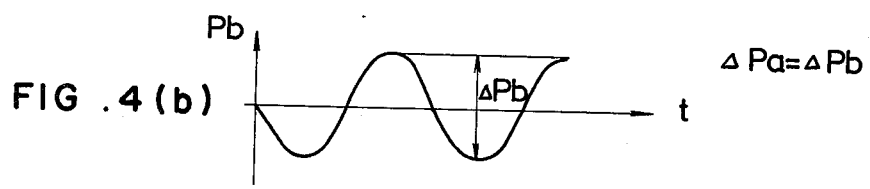
FIG. 4(b)  $\Delta Pa = \Delta Pb$
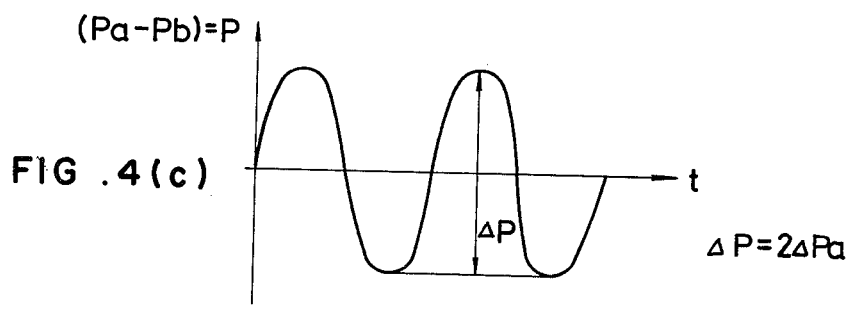
FIG. 4(c)  $\Delta P = 2\Delta Pa$

GAS ANALYZER

BACKGROUND OF THE INVENTION

The present invention relates to gas analysers, such as an infrared (ray) gas analyser of the non-dispersion type or an ultraviolet (ray) gas analyser, which are used for measuring the concentration of carbon monoxide or the like in the air.

Convenional infrared gas analysers of the non-dispersion type are shown in FIG. 1 and FIG. 2. FIG. 1 shows a gas analyser of the non-dispersion type which adopts a method employing a double light path and intermittant light and which consists of light source 44, 44, revolving sector 45, reference cell 46, measurement cell 47 and detector 41. Although various kinds of detector 41 have been used, the present discussion will make reference to a pneumatic detector using a condenser microphone. In order to eliminate the influence of a change in the surrounding temperature upon detector 41, the separated right and left rooms 42a and 42b, respectively, are communicated by an aperture or leak 43 so that the pressure therebetween will always be at a static equilibrium and thus detector 41 will sense only dynamic pressure changes having short cycles. In order to realize this, there is installed a revolving sector 45 which intermittently passes an infrared ray emitted from light source 44, 44 at constant intervals. Furthermore, gases such as nitrogen which do not absorb infrared rays are enclosed in reference cell 46. Zero gas is put into sampling cell 47, and then the energy of the infrared rays reaching the right and left rooms 42a and 42b of detector 41 are balanced and their phases are so equalized that the output of detector 41 is adjusted to zero. Then, the test gas is put into sampling cell 47. If the test gas absorbs the energy of infrared rays while the rays pass through sampling cell 47, a difference occurs between the energy of the infrared rays which pass through sampling cell 47 and of the infrared rays which pass through reference cell 46. This difference of energies leads to the generation of an unbalanced pressure signal synchronized with the cycles of revolving sector 55 between room 42b and room 42a of detector 41. Such signal is amplified and indicated on indicator 48 as a measurement of the concentration of the specified gaseous component in the test gas.

However, in this method a slight break or change in the energy balance between right room 42a and left room 42b of the optical system eliminates stability in a highly sensitive region. The reasons why this method is not suitable for measuring a particularly small amount of a gaseous component are because a remarkably high precision is required to maintain a balance of energy, an equalization of phases or the like (zero adjustment of detector 41), the adjustment is troublesome and time-consuming and furthermore an expensive apparatus is required for carrying out the adjustment. In addition to the above, an additional problem exists with regard to maintenance because the device has mechanically movable parts.

FIG. 2 shows a single light path gas analyser of the non-dispersion type in which the light intermittent method is not adopted without using a reference cell and a revolving chopper described in the above mentioned example. In this arrangement, 51 is a sampling cell and 58 is a detector. Although various kinds of detector 48 have been used, the present discussion will make reference to a pneumatic detector. The test gas and the standard gas (for example, zero gas) are alternately put into sampling cell 51 by operating pressure regulators 53a, 53b and needle valves 54a, 54b, respectively, in addition to by alternately opening and closing three-way electro-magnetic valves 52a, 52b. Infrared rays emitted from a light source 55 are not absorbed while the sampling cell is filled with zero gas. On the other hand, the special gaseous component in test gas absorbs infrared rays when the test gas is put into sampling cell 51, and thus a condenser membrane 57 provided in the separated room 56 is pressurized. The static capacity of the condenser is altered at a constant cycle synchronized with a change-over cycle of three-way electro-magnetic valves 52a, 52b. The concentration of the gaseous component is measured by electrically measuring such change in the static capacity of the condenser.

But, although this single-cell type device can overcome to some degree the defects of the above mentioned prior art gas analyser of FIG. 1, the length of the sampling cell must be increased in order to measure special gaseous components which are contained in particularly small amounts in the test gas because the quantity of infrared rays absorbed is in proportion to the length of the cell and thus also the space for receiving gas in the sampling cell 51 is increased. Therefore, the quantity of the test gas or zero gas put into sampling cell 51 is increased enormously for the measurement of small amounts of gaseous components. For example, in the measurement of carbon monoxide in air, a length L of the cell of 30 to 50 cm and a space V for receiving gas of 90 to 150 cm$^3$ are normally required. If a frequency of 5 Hz is used in detector 58, the test gas or zero gas must be put into sampling cell 51 at a ratio of 27 to 45 liters/-min. Thus, a pump of a great capacity is required and therefore a large scale apparatus is required. This leads to the problem of large costs. A gas analyser of this type has the defect in that it has no practical use because a supply of zero gas of a great volume is required in addition to the above mentioned troublesome problems.

SUMMARY OF THE INVENTION

The object of the present invention is to provide a practical gas analyser which can measure special gaseous components in a test gas with a remarkable precision owing to its high stability and good operability, and in particular which can effectively measure gaseous components of a small amount in order to overcome the disadvantages of the above mentioned prior art gas analysers.

BRIEF DESCRIPTION OF THE DRAWINGS

Other objects and advantages of the invention will appear more clearly from the following description in connection with the accompanying drawings, in which:

FIG. 3 is a schematic illustration of a first embodiment of the invention.

FIGS. 4 (a) to (c) are graphs showing the output of the detector.

DETAILED DESCRIPTION OF THE PREFERRED EMBODIMENTS

Figure 1:
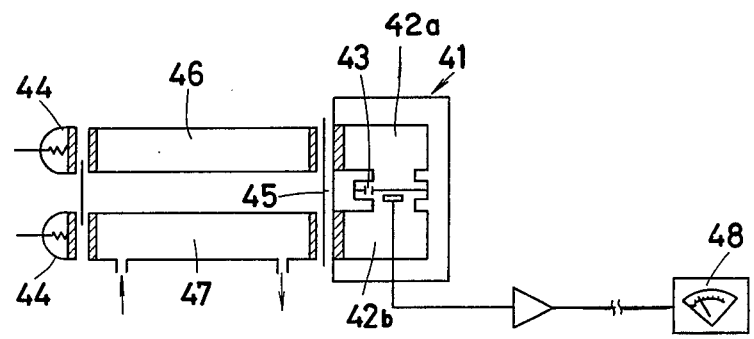
FIGS. 1 and 2 are schematic illustrations of the above discussed conventional gas analysers.
Figure 2:
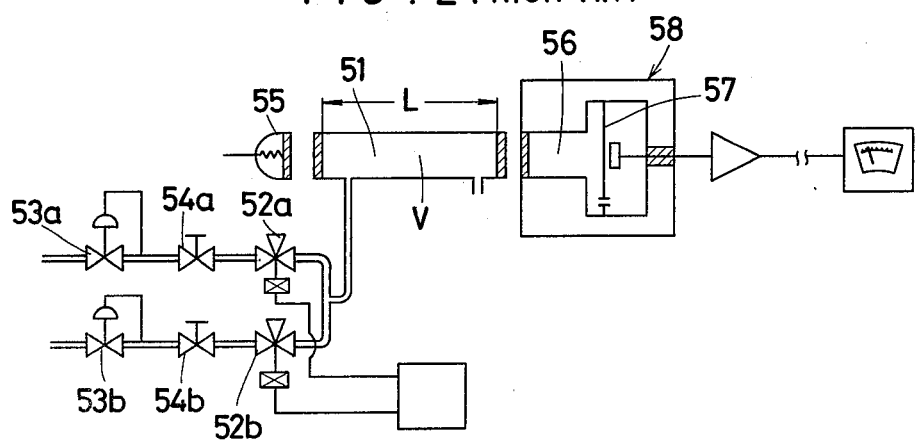

An infrared gas analyser will now be described according to one embodiment of the invention as follows.

FIG. 3 shows a first example of the invention, in which the test gas and the standard gas are introduced into a cell portion E consisting of a first cell 7 and a second cell 8 and then are detected in a detecting portion F after passing through an introducing portion C and a flowing path changing-over portion D and being changed-over at constant intervals. Explaining in more detail, pressure regulators 3a, 3b, needle valves 4a, 4b and three-way electromagnetic valves 5a, 5b are successively arranged in series in this order from upstream portions of a first gas flowing path 1 and a second gas flowing path 2 respectively having inlets A and B. The first gas flowing path 1 and the second gas flowing path 2 are connected with an inlet 7a and 8a, respectively, of the first cell 7 and the second cell 8 which also have respective exits 7b and 8b. A third gas flowing path 9 branches from first gas flowing path 1 at a position downstream of three-way electromagnetic valve 5a, and third gas flowing path 9 is connected with three-way electromagnetic valve 5b. Similarly, a fourth gas flowing path 10 branches from second gas flowing path 2 at a position downstream of three-way electromagnetic valve 5b, and fourth gas flowing path 10 is connected with three-way electromagnetic valve 5a. 11 is a detector. 16 and 17 are an amplifier and an indicator, respectively. Detector 11 must be any suitable type of detector selected depending on the kind of light to be detected. For example, an infrared detector is used for infrared rays, and an ultraviolet detector is used for ultraviolet rays. An infrared detector will be referred to in this discussion. Although the infrared detector can be a solid detector in which a pyroelectric couple, semiconductive couple, thermoelectric couple or the like is used, the present discussion will refer to a pneumatic detector in which a condenser microphone is used. A condenser membrane 13 having a leak 12 is extended between and separates rooms a and b which respectively receive the rays from light sources 6a and 6b through cells 7 and 8. Membrane 13 forms one electrode or pole of a condenser. A fixed pole 14 is arranged as the other pole or electrode of the condenser at a position facing condenser membrane 13. Fixed pole 14 is connected with an amplifier 16 and an indicator 17 through a lead wire 15.

A controller 18 controls the changing-over action of three-way electromagnetic valves 5a, 5b. Infrared rays pass through windows 19, and 20 is insulation.

In such construction, the test gas and the standard gas (for example, zero gas such as nitrogen or the like) are continuously introduced through inlet A and inlet, B respectively. At first a signal from controller 18 starts the action of three-way electromagnetic valves 5a, 5b to open a portion 1a of gas flowing path 1 located upstream of three-way electromagnetic valve 5a into a gas flowing path portion 1b located downstream of three-way electromagnetic valve 5a and simultaneously to open a portion 2a of gas flowing path 2 located upstream of three-way electromagnetic valve 5b into a gas flowing path portion 2b located downstream of three-way electromagnetic valve 5b. As a result, the test gas and zero gas are introduced and filled into first cell 7 and second cell 8, respectively. Then a signal from controller 18 changes-over the three-way electromagnetic valves 5a, 5b to open gas flowing path portion 1a into the fourth gas flowing path 10 and simultaneously to open gas flowing path portion 1b into the third gas flowing path 9. As a result, the test gas and zero gas are introduced into second cell 8 and first cell 7, respectively. The initially introduced test gas and zero gas are discharged from first cell 7 and second cell 8 outside of the analyser through exits 7b and 8b, respectively. Thus, zero gas and test gas are now filled into first cell 7 and second cell 8, respectively. At this time, the amount of the flowing test gas and zero gas is fixedly regulated by using pressure regulators 3a, 3b and needle valves 4a, 4b respectively.

In the case when zero gas is introduced simultaneously into both cells 7 and 8, infrared rays emitted from light sources 6a, 6b are not absorbed and therefore detector 11 shows an output of 0. But, as the different gases are alternately filled into both cell 7 and 8 at fixed intervals and fixed amounts by the repetition of the above mentioned operations, the energy of infrared rays is absorbed by the special gaseous components contained in the test gas in first cell 7 in the same way as in a gas analyzer of a single cell type, and the pressure Pa inside separated room a detector 11 shows the change as shown in FIG. 4 (a), wherein t is time and $\Delta Pa$ is the amount of the displacement of Pa, while the pressure Pb inside separated room 5 shows the change as shown in FIG. 4 (b), because zero gas and the test gas are alternately introduced into second cell 8 in the same way as first cell 7. Besides, the pressures Pa and Pb are equalized with regard to their amounts of displacements and have a difference of a half cycle in their phases. Therefore, the pressure acting on condenser membrane 13 is a difference between the pressure Pa inside separated room a and the pressure Pb inside separated room b, $P = Pa - Pb$ (see FIG. 4 (c)). This difference of the pressure leads to an alternation in the static capacity of the condenser. This alteration in the static capacity of the condenser is transformed into an electric signal, and then the concentration of the special gaseous component contained in the test gas can be read by multiplying such electric signal with amplifier 16 and reading a multiplied electric signal on indicator 17.

Figure 5A:
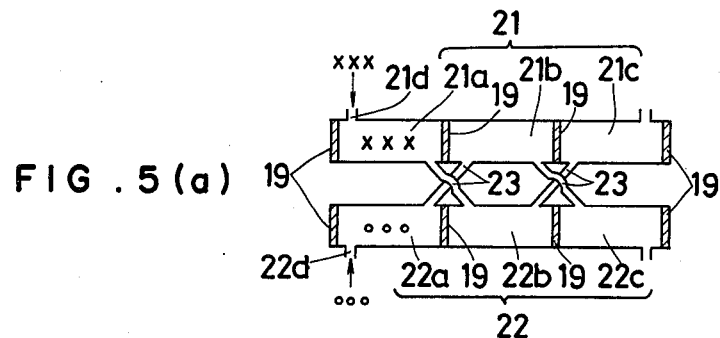
FIGS. 5 (a) to (d) are schematic illustrations of a second embodiment of the invention.
Figure 5B:
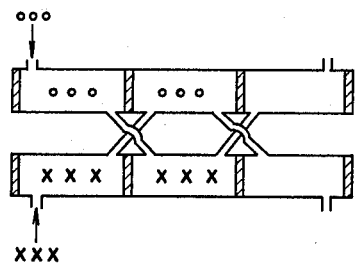
Figure 5C:
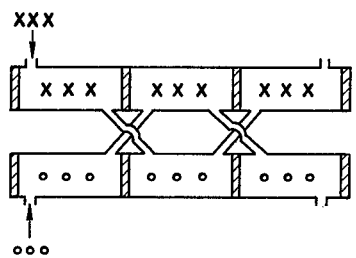
Figure 5D:
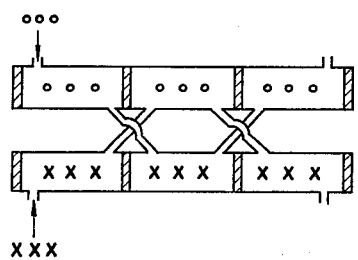

FIGS. 5 (a) to (d) show a second example of the invention. The portion of FIG. 3 designated $\alpha$ is constructed as follows. The first cell 21 and the second cell 22 are each divided into plural chambers 21a—and 22a—by windows 19 through which infrared rays pass. As shown in the figures, chamber 21a, chamber 21b, chamber 22a and chamber 22b open into and communicate with chamber 22b, chamber 22c, chamber 21b, chamber 21c, respectively, through pipes 23. If the test gas of the same amount as the volume of one chamber inside the cell is introduced into chamber 21s through an inlet 21d (shown by xxx in FIG. 5 (a)) and zero gas of the same amount as the volume of one chamber inside the cell is introduced into chamber 22a through an inlet 22d (shown by ooo in FIG. 5 (a)), and then zero gas and the test gas are introduced into chamber 21a and chamber 22a by changing-over three-way electromagnetic valves 5a, 5b, respectively the test gas and zero gas initially introduced are discharged into chambers 21b and 22b, respectively. Thus, the state as shown in FIG. 5 (b) is formed. Then, if the test gas and zero gas are introduced into chamber 21a and chamber 22a by again changing-over three-way electromagnetic valves 5a, 5b, the state as shown in FIG. 5 (c) is formed, that is to say, the test gas and zero gas are filled into first cell 21 and second cell 22, respectively. The following repetition of the above mentioned operations leads to the state as shown in FIG. 5 (d), that is to say, zero gas and the test gas are filled into first cell 21 and second cell 22, respectively, Further repetition of the above mentioned operations leads to the formation of the state as shown in FIG. 5(c), that is to say, the test gas and zero gas are alternately introduced into first cell 21, while zero gas and the test gas are alternately introduced into second cell 22. At such time, the difference of the pressure acting on condenser membrane 13 shows the same alteration as shown in FIG. 4(c). The number of the chambers 21a—,22a—may be optionally selected in dependence upon the diffusion of the gas or the like.

Moreover, in each embodiment mentioned above, infrared rays were used. But, ultraviolet rays may also be used and in this case a window which passes ultraviolet rays is used instead of a window which passes infrared rays. The detector 11 maybe of the mass-flow type or the solid type in addition to the pneumatic type. Only one light source may be employed.

The above mentioned construction of the invention leads to the following effects.

The test gas and the standard gas are introduced into two cells at fixed intervals and fixed amounts, and as a result the pressures Pa, Pb occur in the separated chambers of the detector and the difference between Pa and Pb, that is to say (Pa—Pb), acts upon the condenser membrane. At this time, as shown clearly in FIGS. 4(a) to (c), the difference of the pressure (a)-(b) can double the strength of the signal for an identical concentration of a gaseous component in comparison with the conventional gas analysers, because the pressures Pa and Pb are identical with regard to their amounts of displacement and because they have a difference of a half cycle in their phases. In other words, the gas analyser according to the present invention has a wider range of measurement than conventional gas analysers in which a low concentration of a gaseous component can be stably measured. Besides, the length of the cells can be reduced by half for the identical concentration of a gaseous component, and thus the apparatus can be miniaturized. In addition to the above, the size of the space for receiving gas in the cells and the amount of the test gas and the standard gas to be introduced into the cells can be reduced by half, and the pump for transferring gas also can be of a reduced capacity. Owing to the above mentioned features, the gas analyser of the present invention can display its great power, especially in the measurement of a gaseous component of a small amount contained in the test gas, for example in the measurement of the concentration of noxious gases contained in the air. Furthermore, the supply of a great volume of zero gas is not required, and therefore the gas analyser of the present invention is remarkably superior in its practical use.

Further, as shown in the above mentioned second embodiment, the division of each cell into plural chambers leads to a further reduction of the amount of flow of the gas and of the elongation of the length of the cell, and thus the above stated effects are still further promoted.

What is claimed is:

1. A gas analyzer comprising:
    a first conduit for the supply of a gas to be tested;
    a second conduit for the supply of a standard gas;
    a first cell;
    a second cell;
    gas flow path change-over means, connected to said first and second conduits, for alternating at fixed intervals between a first gas supply arrangement wherein fixed amounts of said gas to be tested and said standard gas are simultaneously supplied to said first and second cells, respectively, and a second gas supply arrangement wherein said fixed amounts of said gas to be tested and said standard gas are simultaneously supplied to said second and first cells, respectively;
    light source means for directing light rays through said first and second cells; and
    detector means for receiving said light rays after passing through said cells.

2. A gas analyzer as claimed in claim 1, wherein said first conduit comprises upstream and downstream portions, said second conduit comprises upstream and downstream portions, said downstream portion of said first conduit is connected to said first cell, and said downstream portion of said second conduit is connected to said second cell, and wherein said changeover means comprises first and second valves between said upstream and downstream portions of said first and second conduits, respectively, a third conduit connecting said second valve and said downstream portion of said first conduit, and a fourth conduit connecting said first valve and said downstream portion of said second conduit.

3. A gas analyzer as claimed in claim 2, wherein each of said first and second valves comprises a three-way electromagnetic valve.

4. A gas analyzer as claimed in claim 1, wherein each of said first and second cells is divided into plural chambers by windows through which said light rays pass, the odd-numbered said chambers of said first cell being connected to the even-numbered said chambers of said second cell, and the odd-numbered said chambers of said second cell being connected to the even-numbered said chambers of said first cell.

* * * * *